United States Patent
Choi et al.

(10) Patent No.: US 10,676,411 B2
(45) Date of Patent: Jun. 9, 2020

(54) OLEFIN CONVERSION PROCESS

(71) Applicant: Lummus Technology Inc., Bloomfield, NJ (US)

(72) Inventors: Sukwon Choi, Clifton, NJ (US); Bala Ramachandran, Easton, PA (US)

(73) Assignee: Lummus Technology Inc., Bloomfield, NJ (US)

( * ) Notice: Subject to any disclaimer, the term of this patent is extended or adjusted under 35 U.S.C. 154(b) by 189 days.

(21) Appl. No.: 15/792,160

(22) Filed: Oct. 24, 2017

(65) Prior Publication Data

US 2018/0057424 A1 Mar. 1, 2018

Related U.S. Application Data

(62) Division of application No. 14/548,475, filed on Nov. 20, 2014, now Pat. No. 9,809,513.

(60) Provisional application No. 61/906,626, filed on Nov. 20, 2013.

(51) Int. Cl.
| | |
|---|---|
| *B01J 8/04* | (2006.01) |
| *C07C 6/04* | (2006.01) |
| *C07C 5/25* | (2006.01) |
| *C07C 11/06* | (2006.01) |
| *C07C 11/08* | (2006.01) |
| *C07C 11/10* | (2006.01) |

(52) U.S. Cl.
CPC .............. *C07C 6/04* (2013.01); *B01J 8/04* (2013.01); *B01J 8/0453* (2013.01); *C07C 5/2512* (2013.01); *C07C 11/06* (2013.01); *C07C 11/08* (2013.01); *C07C 11/10* (2013.01); *B01J 2208/025* (2013.01); *B01J 2219/00006* (2013.01); *C07C 2521/08* (2013.01); *C07C 2521/10* (2013.01); *C07C 2523/30* (2013.01)

(58) Field of Classification Search
None
See application file for complete search history.

(56) References Cited

U.S. PATENT DOCUMENTS

| | | | |
|---|---|---|---|
| 3,636,126 A | 1/1972 | Menapace | |
| 3,761,537 A * | 9/1973 | Homeier | C07C 6/04 585/644 |

(Continued)

OTHER PUBLICATIONS

Office Action issued in corresponding GCC Application No. 2014-28360 dated Jul. 22, 2018 (4 pages).

(Continued)

*Primary Examiner* — Jennifer A Leung
(74) *Attorney, Agent, or Firm* — Osha Liang LLP

(57) ABSTRACT

Processes for the production of olefins are disclosed, which may include: contacting a hydrocarbon mixture comprising linear butenes with an isomerization catalyst to form an isomerization product comprising 2-butenes and 1-butenes; contacting the isomerization product with a first metathesis catalyst to form a first metathesis product comprising 2-pentene and propylene, as well as any unreacted $C_4$ olefins, and byproducts ethylene and 3-hexene; and fractionating the first metathesis product to form a C3-fraction and a C5 fraction comprising 2-pentene. The 2-pentene may then be advantageously used to produce high purity 1-butene, 3-hexene, 1-hexene, propylene, or other desired products.

13 Claims, 11 Drawing Sheets

(56) References Cited

U.S. PATENT DOCUMENTS

| | | | | |
|---|---|---|---|---|
| 4,684,760 A * | 8/1987 | Drake | ................. | B01J 21/10 |
| | | | | 585/664 |
| 5,698,760 A * | 12/1997 | Kelly | ................. | C07C 6/04 |
| | | | | 585/324 |
| 5,905,055 A | 5/1999 | Verdonck et al. | | |
| 5,990,369 A | 11/1999 | Barger et al. | | |
| 6,271,430 B2 * | 8/2001 | Schwab | ................. | B01D 3/141 |
| | | | | 585/313 |
| 6,433,240 B1 | 8/2002 | Schwab et al. | | |
| 6,538,168 B1 * | 3/2003 | Schwab | ................. | C07C 7/005 |
| | | | | 585/324 |
| 6,884,917 B1 | 4/2005 | Coleman | | |
| 8,178,736 B2 | 5/2012 | Gartside et al. | | |
| 2001/0003140 A1 | 6/2001 | Schwab et al. | | |
| 2002/0019790 A1 | 2/2002 | Edgar et al. | | |
| 2002/0197190 A1 | 12/2002 | Schwab et al. | | |
| 2003/0176754 A1 | 9/2003 | Gartside et al. | | |
| 2010/0099934 A1 | 4/2010 | Gartside et al. | | |
| 2011/0034747 A1 | 2/2011 | Gartside et al. | | |
| 2011/0263917 A1 | 10/2011 | Van Hal et al. | | |
| 2012/0316057 A1 | 12/2012 | Taoufik et al. | | |

OTHER PUBLICATIONS

International Serarch Report and Written Opinion dated Feb. 10, 2015 in corresponding International Application No. PCT/US2014/066410 (9 pages).
Notification of First Office Action dated Nov. 17, 2016 in corresponding Chinese application No. 201480062787.2 (w/ translation) (24 pages).

* cited by examiner

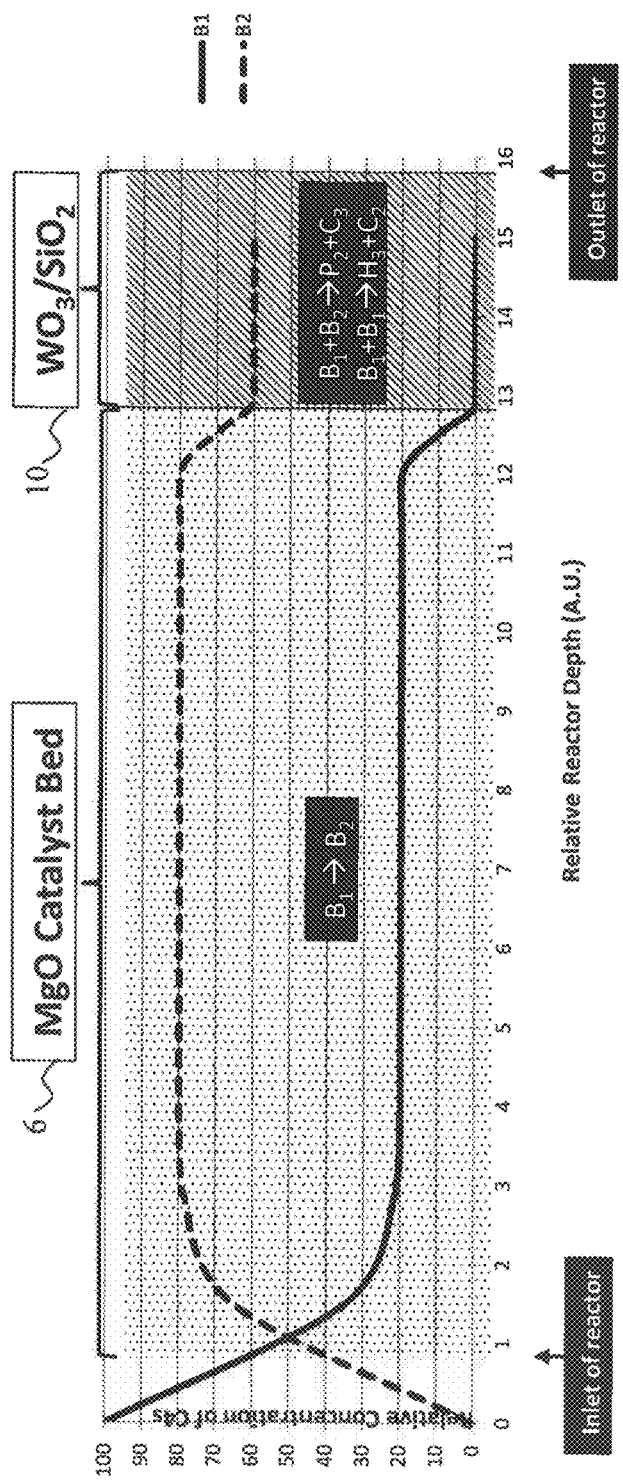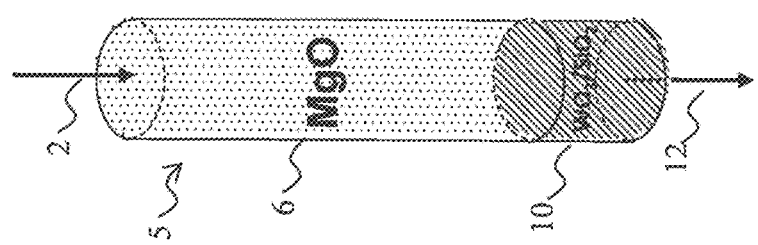

OLEFIN CONVERSION PROCESS

BACKGROUND OF DISCLOSURE

Field of the Disclosure

Embodiments disclosed herein relate generally to the production of high purity alpha-olefins, such as $C_4$ to $C_8$ olefins, for use in various downstream processes, such as use as a co-monomer in the production of polyethylenes and polypropylenes, among other end uses. More specifically, embodiments disclosed herein relate to the more efficient production and purification of alpha-olefins utilizing isomerization and metathesis.

Background

Processes for producing high purity polymer-grade comonomers include various 1-butene comonomer production processes and 1-hexene comonomer production processes. These processes utilize metathesis and/or double-bond isomerization reactions that occur over specific catalysts using mixed n-butenes as the feed to produce polymer-grade 1-butene and 1-hexene used as comonomers for production of polyethylene. However, these processes are extremely energy intensive as they employ distillation to separate the desired alpha-olefin (1-butene and 1-hexene) with high purity from mixtures of their positional isomers that exhibit very close boiling points (2-butene and 2-hexene, 3-hexene, respectively).

For example, the 1-butene process flow includes a butenes superfractionator that separates the 1-butene product from 2-butene. The 1-hexene process is even more energy intensive as it requires two superfractionators: a butenes superfractionator to separate a high-purity 1-butene stream used to produce hexenes, and a hexenes superfractionator to separate the final 1-hexene product from the other positional hexene isomers (2-hexene and 3-hexene).

The high operating costs associated with the energy intensive distillation towers in the processes have significantly hampered the commercialization efforts for these processes, especially for the 1-hexene process that requires two (2) superfractionators.

SUMMARY OF THE DISCLOSURE

In one aspect, embodiments disclosed herein relate to a process for the production of olefins. The process may include: contacting a hydrocarbon mixture comprising linear butenes with an isomerization catalyst to form an isomerization product comprising 2-butenes and 1-butenes, contacting the isomerization product with a first metathesis catalyst to form a first metathesis product comprising 2-pentene and propylene, as well as any unreacted $C_4$ olefins, and byproducts ethylene and 3-hexene; and fractionating the first metathesis product to form a C3-fraction and a C5 fraction comprising 2-pentene.

For the production of 1-butene and/or propylene, the process may also include: (d) contacting ethylene and the C5 fraction with a second metathesis catalyst, which may be the same or different than the first metathesis catalyst, to convert at least a portion of the 2-pentene and ethylene to propylene and 1-butene and form a second metathesis product. The second metathesis product may then be fractionated to form a propylene fraction and a 1-butene fraction. The 1-butene fraction may have a purity of at least 98 wt % 1-butene.

For the production of 3-hexene and/or 1-hexene, the process may also include: contacting the C5 fraction with a second metathesis catalyst, which may be the same or different than the first metathesis catalyst, to convert at least a portion of the 2-pentene to 2-butene and 3-hexene and form a second metathesis product. The second metatheses product may then be fractionated to form a 2-butene fraction and a 3-hexene fraction. The 3-hexene fraction may have a purity of at least 98 wt % 3-hexene. To produce 1-hexene, the process may also include a step for converting the 3-hexene fraction via isomerization to 1-hexene.

In another aspect, embodiments disclosed herein relate to a process for the production of olefins. The process may include: feeding a mixed C4-olefin stream comprising a mixture of 1-butene and 2-butene to an isomerization/metathesis reactor including a first reaction zone comprising an isomerization catalyst and a second reaction zone comprising a first metathesis catalyst; contacting the C4-olefin stream with the isomerization catalyst in the first reaction zone to form an isomerization product comprising 2-butene and 1-butene; contacting the isomerization product with the metathesis catalyst in the second reaction zone to form a first metathesis product comprising 2-pentene, propylene, and byproducts ethylene and 3-hexene; feeding the first metathesis product to a fractionation system; fractionating the first metathesis product in the fractionation system to form at least one C3-fraction and a C5 fraction comprising 2-pentene.

In another aspect, embodiments disclosed herein relate to a process for the production of olefins. The process may include: feeding a mixed C4-olefin stream comprising a mixture of 1-butene and 2-butene to an isomerization/metathesis reactor including a first reaction zone comprising an isomerization catalyst and a second reaction zone comprising a first metathesis catalyst; contacting the C4-olefin stream with the isomerization catalyst in the first reaction zone to form an isomerization product comprising 2-butene and 1-butene; contacting the isomerization product with the metathesis catalyst in the second reaction zone to form a first metathesis product comprising 2-pentene, propylene, and byproducts ethylene and 3-hexene; feeding the first metathesis product to a fractionation system; fractionating the first metathesis product in the fractionation system to form at least one C3-fraction and a C5 fraction comprising 2-pentene; feeding ethylene and the C5 fraction to a metathesis reactor and contacting the 2-pentene with a second metathesis catalyst, which may be the same or different than the first metathesis catalyst, to convert at least a portion of the ethylene and 2-pentene to propylene and 1-butene and recovering a second metathesis product; fractionating the second metathesis product to recover a propylene fraction and a 1-butene fraction.

In another aspect, embodiments disclosed herein relate to a process for the production of olefins. The process may include: feeding a mixed C4-olefin stream comprising a mixture of 1-butene and 2-butene to an isomerization/metathesis reactor including a first reaction zone comprising an isomerization catalyst and a second reaction zone comprising a first metathesis catalyst; contacting the C4-olefin stream with the isomerization catalyst in the first reaction zone to form an isomerization product comprising 2-butene and 1-butene; contacting the isomerization product with the metathesis catalyst in the second reaction zone to form a first metathesis product comprising 2-pentene, propylene, and byproducts ethylene and 3-hexene; feeding the first metathesis product to a fractionation system; fractionating the first metathesis product in the fractionation system to form at least one C3-fraction and a C5 fraction comprising 2-pentene; feeding the C5 fraction to a metathesis reactor and contacting the 2-pentene with a second metathesis catalyst, which may be the same or different than the first metathesis catalyst, to convert at least a portion of the 2-pentene to 2-butene and 3-hexene and recovering a second metathesis product; fractionating the second metathesis product to recover a 2-butene fraction and a 3-hexene fraction.

In another aspect, embodiments disclosed herein relate to a process for the production of olefins. The process may include: feeding a mixed C4-olefin stream comprising a mixture of 1-butene and 2-butene to an isomerization/metathesis reactor including a first reaction zone comprising an isomerization catalyst and a second reaction zone comprising a first metathesis catalyst; contacting the C4-olefin stream with the isomerization catalyst in the first reaction zone to form an isomerization product comprising 2-butene and 1-butene; contacting the isomerization product with the metathesis catalyst in the second reaction zone to form a first metathesis product comprising 2-pentene, propylene, and byproducts ethylene and 3-hexene; feeding the first metathesis product to a fractionation system; fractionating the first metathesis product in the fractionation system to form an ethylene fraction, a propylene fraction, a C4 fraction and a C5+ fraction comprising 2-pentene and 3-hexene; feeding ethylene and the C5 fraction to a metathesis reactor and contacting the 2-pentene with a second metathesis catalyst, which may be the same or different than the first metathesis catalyst, to convert at least a portion of the ethylene and 2-pentene to propylene and 1-butene and to convert at least a portion of the 3-hexene and ethylene to 1-butene and recovering a second metathesis product; feeding the second metathesis product to the fractionation system.

In another aspect, embodiments disclosed herein relate to a system for the production of olefins. The system may include: an isomerization/metathesis reaction system for: contacting a hydrocarbon mixture comprising linear butenes with an isomerization catalyst to form an isomerization product comprising 2-butenes and 1-butenes; and contacting the isomerization product with a first metathesis catalyst to form a first metathesis product comprising 2-pentene and propylene, as well as any unreacted $C_4$ olefins, and byproducts ethylene and 3-hexene; a fractionation system for fractionating the first metathesis product to form a C3-fraction and a C5 fraction comprising 2-pentene.

In another aspect, embodiments disclosed herein relate to a system for the production of olefins. The system may include: an isomerization/metathesis reactor including an inlet for feeding a mixed C4-olefin stream comprising a mixture of 1-butene and 2-butene and including a first reaction zone comprising an isomerization catalyst and a second reaction zone comprising a first metathesis catalyst for: contacting the C1-olefin stream with the isomerization catalyst in the first reaction zone to form an isomerization product comprising 2-butene and 1-butene; contacting the isomerization product with the metathesis catalyst in the second reaction zone to form a first metathesis product comprising 2-pentene, propylene, and byproducts ethylene and 3-hexene. The system may also include: a fractionation system for fractionating the first metathesis product to form at least one C3-fraction and a C5 fraction comprising 2-pentene.

In another aspect, embodiments disclosed herein relate to a system for the production of olefins. The system may include: an isomerization/metathesis reactor including an inlet for feeding a mixed C1-olefin stream comprising a mixture of 1-butene and 2-butene and including a first reaction zone comprising an isomerization catalyst and a second reaction zone comprising a first metathesis catalyst for: contacting the C4-olefin stream with the isomerization catalyst in the first reaction zone to form an isomerization product comprising 2-butene and 1-butene; contacting the isomerization product with the metathesis catalyst in the second reaction zone to form a first metathesis product comprising 2-pentene, propylene, and byproducts ethylene and 3-hexene. The system may also include: a fractionation system for fractionating the first metathesis product to form at least one C3-fraction and a C5 fraction comprising 2-pentene; a metathesis reactor and contacting ethylene and the 2-pentene in the C5 fraction with a second metathesis catalyst, which may be the same or different than the first metathesis catalyst, to convert at least a portion of the ethylene and 2-pentene to propylene and 1-butene and recovering a second metathesis product; and a second fractionation system for fractionating the second metathesis product to recover a propylene fraction and a 1-butene fraction.

In another aspect, embodiments disclosed herein relate to a system for the production of olefins. The system may include: an isomerization/metathesis reactor including an inlet for feeding a mixed C4-olefin stream comprising a mixture of 1-butene and 2-butene and including a first reaction zone comprising an isomerization catalyst and a second reaction zone comprising a first metathesis catalyst for: contacting the C4-olefin stream with the isomerization catalyst in the first reaction zone to form an isomerization product comprising 2-butene and 1-butene; contacting the isomerization product with the metathesis catalyst in the second reaction zone to form a first metathesis product comprising 2-pentene, propylene, and byproducts ethylene and 3-hexene. The system may also include: a first fractionation system for fractionating the first metathesis product to form at least one C3-fraction and a C5 fraction comprising 2-pentene; a metathesis reactor for contacting the 2-pentene in the C5 fraction with a second metathesis catalyst, which may be the same or different than the first metathesis catalyst, to convert at least a portion of the 2-pentene to 2-butene and 3-hexene and recovering a second metathesis product; and a second fractionation system for fractionating the second metathesis product to recover a 2-butene fraction and a 3-hexene fraction. The system may also include a flow conduit for diverting the second metathesis product to the first fractionation system, providing system flexibility for the production of propylene only.

In another aspect, embodiments disclosed herein relate to a system for the production of olefins. The system may include: an isomerization/metathesis reactor including an inlet for feeding a mixed C4-olefin stream comprising a mixture of 1-butene and 2-butene and including a first reaction zone comprising an isomerization catalyst and a second reaction zone comprising a first metathesis catalyst for: contacting the C4-olefin stream with the isomerization catalyst in the first reaction zone to form an isomerization product comprising 2-butene and 1-butene; contacting the isomerization product with the metathesis catalyst in the second reaction zone to form a first metathesis product comprising 2-pentene, propylene, and byproducts ethylene and 3-hexene. The system may also include: a fractionation system for fractionating the first metathesis product to form an ethylene fraction, a propylene fraction, a C4 fraction and a C5+ fraction comprising 2-pentene and 3-hexene; a metathesis reactor for contacting ethylene and the C5 fraction with a second metathesis catalyst, which may be the same or different than the first metathesis catalyst, to convert at least a portion of the ethylene and 2-pentene to propylene and 1-butene and to convert at least a portion of the 3-hexene and ethylene to 1-butene and recovering a second metathesis product; and a flow conduit for feeding the second metathesis product to the fractionation system.

Other aspects and advantages will be apparent from the following description and the appended claims.

BRIEF DESCRIPTION OF DRAWINGS

FIG. 3 is a simplified process flow diagram of an isomerization/metathesis reactor for use in processes for producing butenes according to embodiments disclosed herein.

FIG. 4 is a chart illustrating the changes in reactant and product equilibrium passing through an isomerization/metathesis reactor according to embodiments disclosed herein.

DETAILED DESCRIPTION

Figure 1:
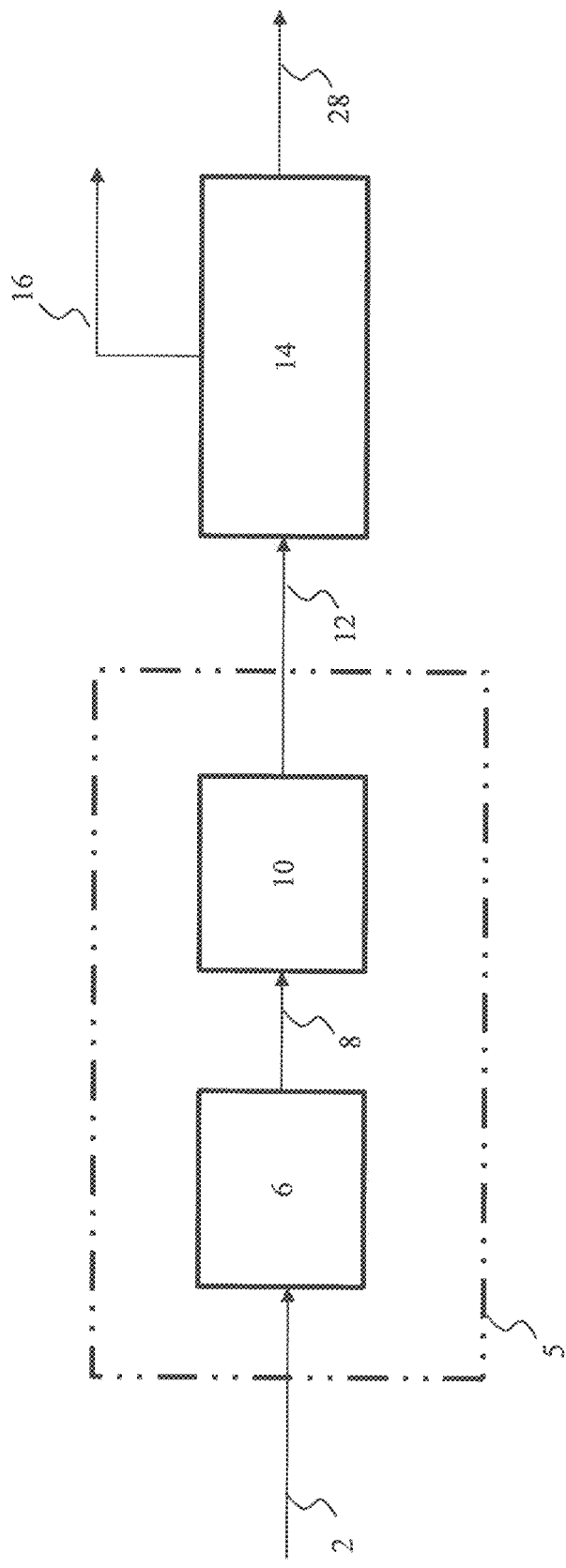
FIG. 1 is a simplified process flow diagram of a process for producing high purity 2-pentenes according to embodiments disclosed herein.

In one aspect, embodiments herein relate to the production of high purity alpha olefins, such as 1-butene and 1-hexene. More specifically, embodiments disclosed herein relate to the more efficient production and purification of alpha-olefins utilizing isomerization and metathesis.

Processes disclosed herein utilize isomerization to favor the production of a high purity beta-olefin, which is easily separable based on carbon number, and that may be used as a chemical intermediate for the production of a high purity alpha-olefin. Embodiments disclosed herein thus eliminate the need of the butenes superfractionator, from 1-butene and 1-hexene processes that, as noted in the Background above, is used to produce a high-purity 1-butene stream from a mixed stream of n-butenes.

The production of a high purity beta-pentene from 1-butene may be achieved in by isomerization and metathesis. The isomerization and metathesis are performed in segregated reaction zones, in the same or different reactors, thus limiting the isomerization and cross-metatheses of the desired intermediate.

For example, when contained in the same reactor, such as a downflow reactor, the segregated reactions may be performed with a catalyst bed configuration including an upper section to perform double-bond isomerization of n-butenes (1-butene and 2-butene) and a lower section to perform cross-metathesis between the formed 1-butene and 2-butene. This catalyst bed configuration allows for the use of any mixture of n-butenes as feed to exclusively produce a high-purity 2-pentene (with essentially no 1-pentene) and propylene stream at high equilibrium product selectivities (>90%) with low levels of ethylene and hexene formation.

The formed 2-pentene stream can be easily separated from co-products propylene, ethylene and 3-hexene without the use of an extensive separation scheme, e.g., superfractionation. This high-purity 2-pentene stream attained may then be further processed to produce high purity streams of 1-butene and 1-hexene.

Embodiments disclosed herein circumvent the need to separate the 1-butene from its positional isomer (2-butene) by distillation in a superfractionator. This is a major improvement for the current comonomer production processes, as it eliminates a highly energy intensive butenes superfractionator from both 1-butene and 1-hexene production processes. This makes the processes to make 1-butene and 1-hexene economically more attractive. Another advantage over the conventional 1-butene and 1-hexene processes embodiments disclosed herein may allow olefin product flexibility, as producers can also withdraw propylene as a by-product, unlike the conventional CPT processes.

For the high purity 1-butene process according to embodiments herein, the exclusive 2-pentene (without 1-pentene) stream is further processed in a metathesis reactor and reacted via cross-metathesis with ethylene to selectively form 1-butene and propylene, which can be easily separated and/or recycled.

For the high purity 1-hexene process according to embodiments herein, the exclusive 2-pentene (without 1-pentene) stream is further processed in a metathesis reactor and reacted via self-metathesis with itself to selectively form 3-hexene and 2-butene, which can be easily separated and recycled to the original n-butenes feed stream. The formed 3-hexene may then undergo further double-bond isomerization to produce a mixture of linear hexenes, which may be fed to a hexenes superfractionation system to separate the 1-hexene product. However, in the overall process, the exclusive 2-pentene production of 1-butene and with itself (self-metathesis) can be easily separated through simple distillation and can be further used in various other process applications (high purity polymer grade 1-butene production and 1-hexene production; isoprene production, etc). Thus, the process reduces the need for the energy intensive separation by distillation of the alpha-olefin from its positional isomers.

Segregated OCU for 2-Pentenes Production

Referring now to FIG. 1, processes according to embodiments herein may produce 2-pentenes via isomerization and metathesis using segregated isomerization and metathesis reaction zones 6, 10, respectively, which may be in the same or different reactors. In some embodiments, the segregated OCU (olefin conversion unit) is a reactor system 5 including an upstream reaction zone 6 to perform double-bond isomerization of n-butenes to form an equilibrium mixture 8 of 1-butene and 2-butenes, followed by a downstream reaction zone 10 to perform cross-metathesis between the formed 1-butene and 2-butene products from the reaction zone 6. This segregated reaction zone configuration allows for the use of any mixture of n-butenes as feed 2 to exclusively produce a constant high-purity 2-pentene (i.e., without 1-pentene) and propylene product stream 12 at high product selectivities (>90%) and with little by-products, i.e., ethylene and hexene. The formed 2-pentene stream 12 can be easily separated from the product mixture without the use of an extensive separation scheme, e.g., superfractionation, such as in a fractionation system 14, which may include a depropylenizer, separating the propylene product 16 from the 2-pentene product 28.

Figure 2:
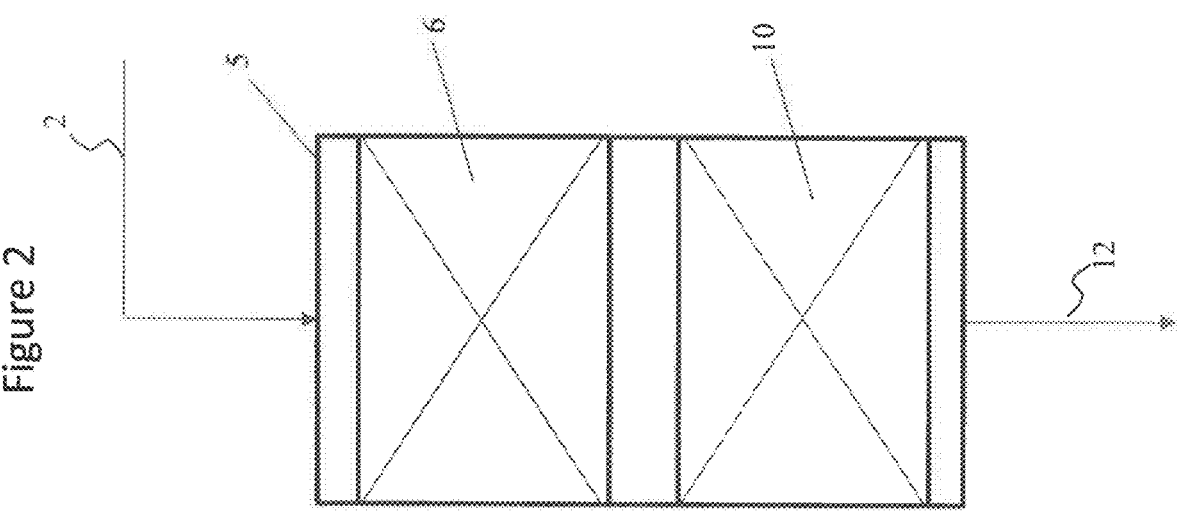
FIG. 2 is a simplified process flow diagram of an isomerization/metathesis reactor for use in processes for producing 1-butene (and/or propylene) or 1-hexene according to embodiments disclosed herein.

In some embodiments, the segregated OCU (olefin conversion unit) is a single downflow reactor 5, such as illustrated in FIG. 2, where like numerals represent like parts. Reactor 5 may include a catalyst bed 6 in the upper portion of the reactor 5 to perform double-bond isomerization of n-butenes to form an equilibrium mixture 8 of 1-butene and 2-butenes, followed by a catalyst bed 10 in the lower portion of the reactor 5 to perform cross-metathesis between the formed 1-butene and 2-butene products from the upper reaction zone 6. This catalyst bed configuration allows for the use of any mixture of n-butenes as feed 2 to exclusively produce a constant high-purity 2-pentene (without 1-pentene) and propylene product stream 12 at high product selectivities (>90%) with little by-products, i.e., ethylene and hexene. The formed 2-pentene stream can be easily separated from the product mixture without the use of an extensive separation scheme, e.g., superfractionation, such as in a fractionation system 14 separating the propylene product 16 from the 2-pentene product 28.

FIG. 3 and FIG. 4 collectively show a schematic representation of one embodiment of the segregated OCU reactor. In this example the feed 2 is a pure 100% 1-butene feed. Catalyst zone 6 includes 4 times more MgO relative to the $WO_3/SiO_2$ metathesis catalyst ($MgO:WO_3/SiO_2=4$) in catalyst zone 10. The upper segregated double-bond isomerization MgO catalyst zone 6 ensures that a constant equilibrium n-butenes mixture maintaining a 2-butene to 1-butene ratio near 4 (B2/B1=4, at 315° C.) is attained at the starting point of the metathesis catalyst bed 10, irrespective of the raw n-butenes feed composition (irrespective of the feed B2/B1 ratio). The relatively higher partial pressure of 2-butene near equilibrium (B2/B1=4 in this example) at the starting point of the metathesis catalyst bed 10 suppresses the unwanted self-metathesis side reaction of the 1-butene to produce ethylene and hexene [B1+B1←→C2+C6] from occurring, which eventually further becomes self-extinguished due to the limited availability of 1-butene as the 1-butene becomes consumed predominantly via the cross-metathesis with 2-butene [B2+B1←→P2+C3], as the self metathesis reaction of 2-butene is non-productive [B2+B2←→B2+B2].

Embodiments herein thus provide an efficient process scheme to convert any mixed linear C4 olefin process streams (varying from pure 1-butene to pure 2-butene) to exclusively produce high purity 2-pentene (without 1-pentene) at near equilibrium compositions. The formed exclusive 2-pentene (without 1-pentene) stream can be easily separated through simple distillation and can be further used in various other process applications (high purity polymer grade 1-butene production and 1-hexene production) as described in the following sections.

In some embodiments, the metathesis product from the isomerization/metathesis reactor may have a 2-pentene to 1-pentene ratio of greater than 100. In other embodiments, the metathesis product from the isomerization/metathesis reactor may have a 2-pentene to 1-pentene ratio of greater than 150, 200, 250, or 300.

Process for Producing High Purity 1-Butene

Figure 5:
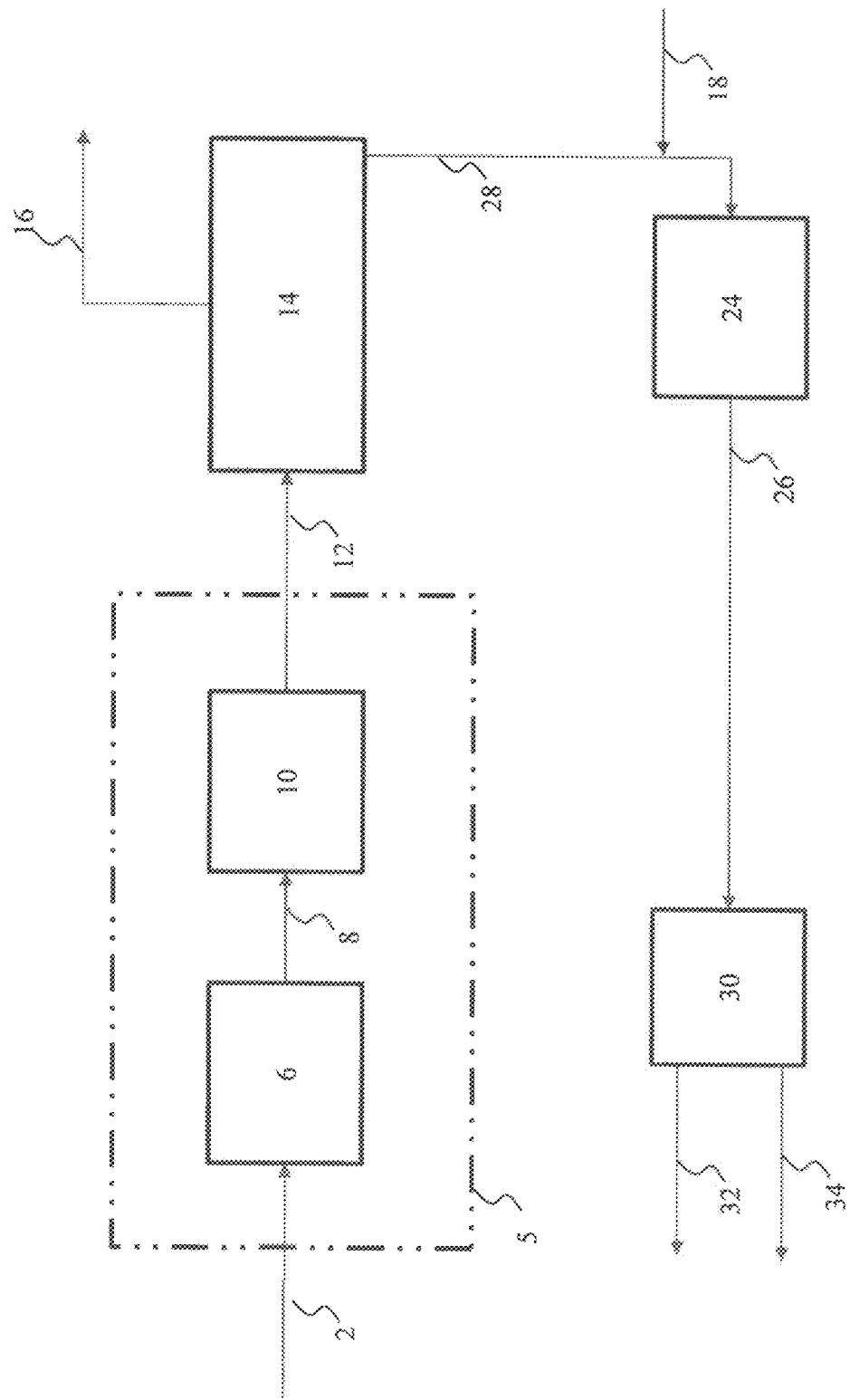
FIG. 5 is a simplified process flow diagram of a process for producing high purity 1-butene according to embodiments disclosed herein.

Referring now to FIG. 5, a simplified process flow diagram for producing high purity 1-butene is illustrated, where like numerals represent like parts. For the 1-butene process, as described above, an exclusive 2-pentene (without 1-pentene) stream 12 is produced from any n-butenes feed stream 2 via reaction in reaction zone 5.

To produce 1-butene, the 2-pentene product stream may be further reacted via cross-metathesis with ethylene 18 in a metathesis reactor 24 to selectively form a product stream 26 including 1-butene and propylene. The metathesis product 26 may then be fed to a fractionation system 30 to separate the propylene from the 1-butene.

In some embodiments, the propylene fraction 32 may be fed to a metathesis reactor, either a separate reactor system, or recycled to reaction zone 5 to produce additional 1-butene. In other embodiments, the propylene fraction 32, or a portion thereof, may be removed as a separate product, depending on the product mixture needs of a specific plant.

In some embodiments, it may be desirable to limit the amount of branched butenes (isobutene) fed to the system. In such an embodiment, the primary feed for this process may be an n-butenes stream free of branched C4 species, such as may be produced from a CD-DeiB™ unit (not shown), used for concurrent isomerization of 1-butene to 2-butene and fractionation of the 2-butene from isobutene (available from Lummus Technology Inc.).

In the upstream double-bond isomerization section of reaction zone 5, double-bond isomerization of the n-butenes (Reaction 1) is the only reaction that occurs, providing an equilibrium mixture of n-butenes at the starting point of the downstream metathesis catalyst bed.

1-Butene←→2-Butene          (Reaction 1)

In the downstream metathesis section of the reaction zone 5, the following reactions occur that produces 2-pentene.

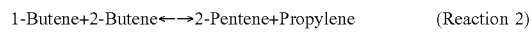

1-Butene+2-Butene←→2-Pentene+Propylene          (Reaction 2)

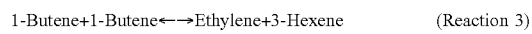

1-Butene+1-Butene←→Ethylene+3-Hexene          (Reaction 3)

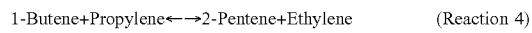

1-Butene+Propylene←→2-Pentene+Ethylene          (Reaction 4)

The isomerization/metathesis reactor effluent is then fed to a primary separation train which may include a deethylenizer, depropylenizer, and debutenizer. The separated 2-pentene (the primary intermediate for 1-butene production) and 3-hexene mixture from the debutanizer bottoms stream is then fed to a metathesis-only reactor with ethylene to form the 1-butene (target a-olefin) product. These reactions can be written as follows.

2-Pentene+Ethylene←→1-Butene+Propylene          (Reaction 5)

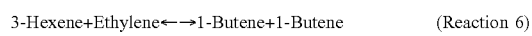

3-Hexene+Ethylene←→1-Butene+1-Butene          (Reaction 6)

The separated propylene may be recycled back along with the recycled C4 stream to the isomerization/metathesis reaction zone or can be drawn as a separate product. Propylene is consumed via Reaction 4 in the isomerization/metathesis reaction zone to produce additional 2-pentene required downstream to ultimately produce the final 1-butene product. The propylene recycle/product split ratio may be used to control the extent of Reaction 4 and is an adjustable parameter that allows additional flexibility to the overall process for co-production of polymer grade propylene in addition to the co-monomer grade 1-butene.

The 1-butene formed from Reaction 5 and Reaction 6 in the metathesis-only reactor (reactor 30) product can now be easily separated from the effluent stream via a secondary separation train that consists of a depropylenizer and debutenizer. This separation train allows the separation of the product 1-butene from the mixture of product propylene and unreacted ethylene, 2-pentene, and 3-hexene feeds that may be recycled if desired (C3's and C4's to the isomerization/metathesis reaction zone, C2's to the metathesis-only reactor).

Ethylene is produced as a by-product from the isomerization/metathesis reaction zone from n-butenes as feed via Reactions 3 and 4 and is not required to be added as a separate feed source for this process scheme. However, optionally fresh ethylene may be added as feed to improve the 1-butene product yields by adjusting the product selectivities in the metathesis-only reactor. One reason for maintaining excess ethylene in the metathesis-only reactor would be to improve the 1-butene product purity by reducing the only possible secondary nonselective reaction pathway that exists to form 2-butene in the metathesis-only reactor that should be avoided in the production of co-monomer grade 1-butene:

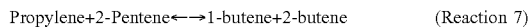
Propylene+2-Pentene⟷1-butene+2-butene (Reaction 7)

This is a secondary reaction that may occur between the propylene formed from Reaction 5 and 2-pentene that enters as feed in the metathesis-only reactor. Depending on the isobutene in the fresh n-butenes to the isomerization/metathesis reaction zone, purges are taken in the C4 and C5+C6 recycle streams to prevent isobutane, isopentene and isohexenes buildup. These purge streams also allow to prevent buildup of any C4, C5, and/or C6 alkanes that have been introduced with the original mixed butenes containing feed.

Figure 6:
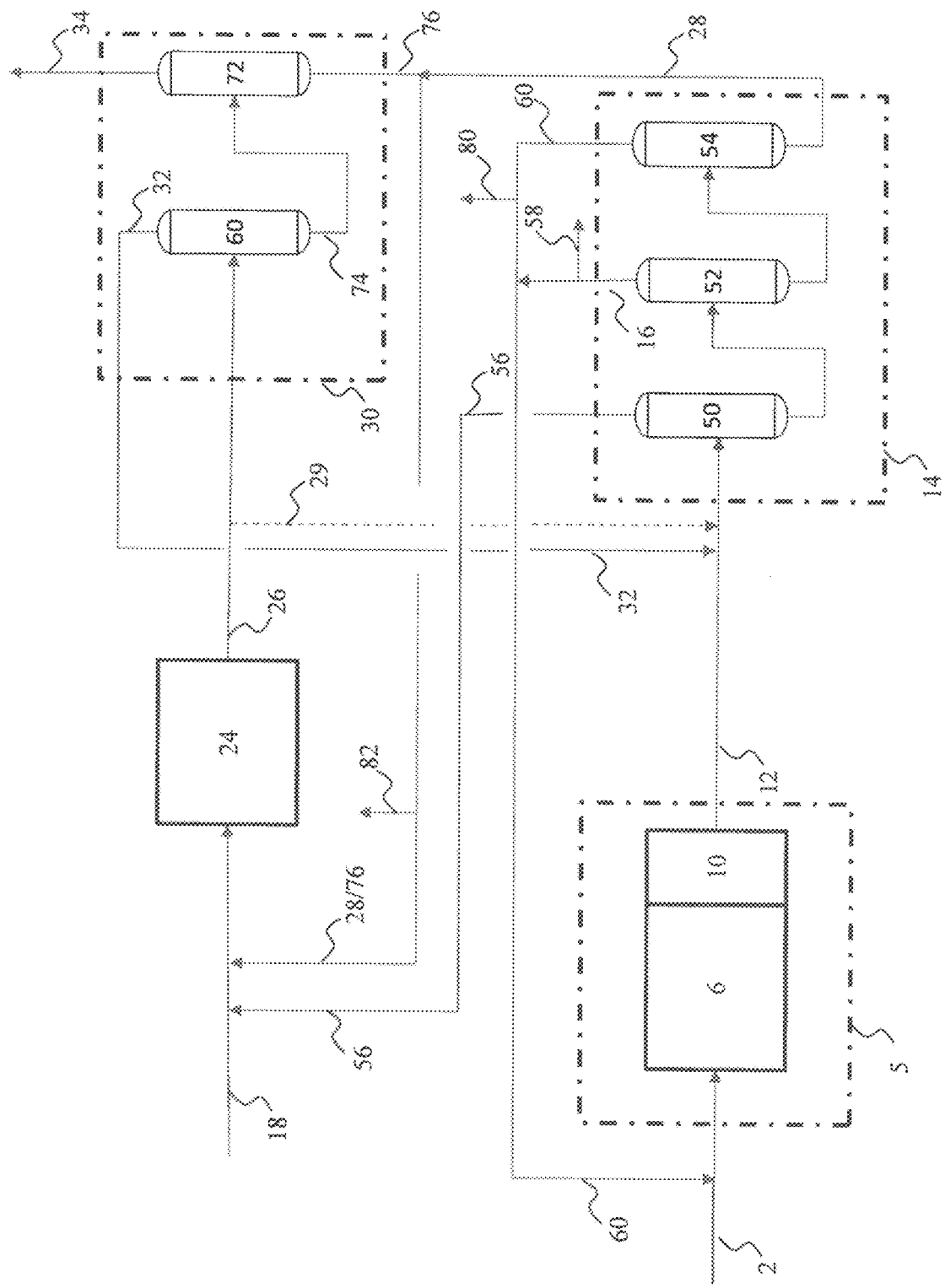
FIG. 6 is a simplified process flow diagram of a process for producing high purity 1-butene according to embodiments disclosed herein.

One embodiment for the overall process to produce high purity 1-butene may be as illustrated in FIG. 6, where like numerals represent like parts. As described above, feed butenes 2, which may be a mixture of normal butenes, pure 1-butene, or pure 2-butene, may be fed to reaction zone 5, including an isomerization zone 6 and a segregated metathesis zone 10, for producing an isomerization/metathesis product 12 including 2-pentene and propylene, as well as some by-product ethylene and 3-hexene.

The isomerization/metathesis product 12 may then be fed to a fractionation system 14 for separation of the products, byproducts, and unreacted reactants (normal butenes). Fractionation system 14 may include a deethylenizer 50, a depropylenizer 52, and a debutenizer 54. The deethylenizer may be used to separate an ethylene fraction 56 from heavier hydrocarbons. The depropylenizer 52 may be used to recover a propylene fraction 16, a portion of which may be recovered as a propylene product 58. The debutenizer 54 may be used to separate a C4 fraction 60 from a fraction 28, including 2-pentenes and any C6's produced.

Fresh ethylene 18, recycled ethylene 56, and 2-pentene fraction 28 may then be fed to metathesis reaction zone 24. In metathesis reaction zone 24, the 2-pentene may react with ethylene to produce 1-butene, and any 3-hexene byproduct from the isomerization/metathesis reaction zone 5 may be reacted with ethylene to additionally produce 1-butene. Effluent 26 may thus include 1-butene (target product), propylene, as well as unreacted 2-pentene, 3-hexene, and ethylene.

The effluent 26 from metathesis reaction zone 24 may then be fed to a fractionation zone 30, which may include a depropylenizer 70 and a debutenizer 72. The depropylenizer 70 may be used to separate a fraction 32 including ethylene and propylene from a bottoms fraction 74. Debutenizer 72 may then be used to separate 1-butene from the unreacted 2-pentene and 3-hexene, where the 1-butene may be recovered as an overheads fraction 34 and the heavies may be recovered as a bottoms fraction 76.

The fraction 32 may be fed to separation system 14 for separation and recovery of ethylene and propylene fractions 56, 16, as described above. Ethylene fraction 56 may be recycled to metathesis reactor 24. Propylene and butene fractions 16 and 60 may be recycled to isomerization/metathesis reaction zone 5. Heavies fraction 76 may also be recycled to metathesis reactor 24 for continued conversion of the C5 and C6 components. As necessary, a C4 purge may be taken via flow stream 80 and a C5/C6 purge may be taken via flow stream 82.

Figure 6A:
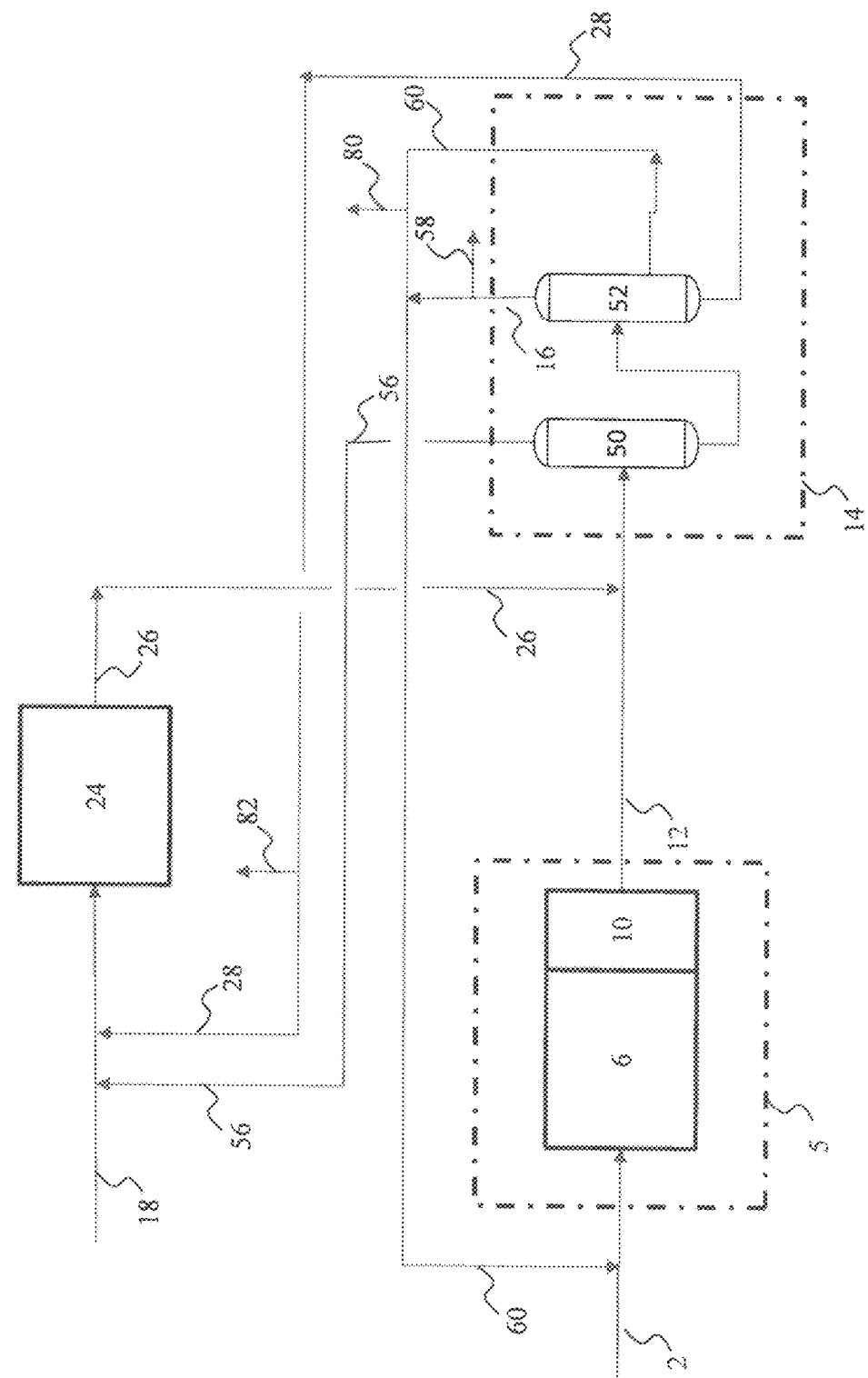
FIG. 6A is a simplified process flow diagram of a process for producing propylene according to embodiments disclosed herein.

In some embodiments, the process of FIG. 6 may be modified, with minor adjustments, to produce propylene as the sole product without any 1-butene, such as illustrated in FIGS. 6 and 6A, where like numerals represent like parts.

Referring now to FIG. 6A, as described above, feed butenes 2, which may be a mixture of normal butenes, pure 1-butene, or pure 2-butene, may be fed to reaction zone 5, including an isomerization zone 6 and a segregated metathesis zone 10, for producing an isomerization/metathesis product 12 including 2-pentene and propylene, as well as some by-product ethylene and 3-hexene.

The isomerization/metathesis product 12 may then be fed to a fractionation system 14 for separation of the products, byproducts, and unreacted reactants (normal butenes). Fractionation system 14 may include a deethylenizer 50 and a depropylenizer 52. The deethylenizer may be used to separate an ethylene fraction 56 from heavier hydrocarbons. The depropylenizer 52 may be used to recover a propylene fraction 16, a portion or all of which may be recovered as a propylene product 58, a C4 fraction 60, which may be recovered as a side draw, and a heavies fraction 28, including 2-pentenes and any C6's produced.

Fresh ethylene 18, as necessary, recycled ethylene 56, and heavies fraction 28 may then be fed to metathesis reaction zone 24. In metathesis reaction zone 24, the 2-pentene may react with ethylene to produce 1-butene, and any 3-hexene byproduct from the isomerization metathesis reaction zone 5 may be reacted with ethylene to additionally produce 1-butene. Effluent 26 may thus include 1-butene, propylene, as well as unreacted 2-pentene, 3-hexene, and ethylene.

The effluent 26 from metathesis reaction zone 24 may then be fed to fractionation system 14, as described above. The butenes produced in metathesis reactor 24 are separated and recycled back to reaction zone 5 to produce propylene. In such an embodiment, significant amounts of propylene may be formed from mixed butenes with little or no externally supplied ethylene.

Referring back to FIG. 6, the process described above, producing propylene 58 and high purity 1-butene stream 34, may be modified to provide flexibility to produce propylene only, similar to that of FIG. 6A, such as to meet added market demand for propylene or when demand for high purity 1-butene is low. In such instances, the second metathesis product 26 recovered from metathesis reactor 24 may be diverted to fractionation system 14 via flow line 29, and fractionation system 30 may be taken off-line. When producing propylene as the primary product, a majority or all of propylene stream 16 may be recovered as product via flow line 58. Suitable valving and control systems may also be included to facilitate the desired process flexibility.

Process for Producing 1-Hexene

As described above with respect to the 1-butenes process, the 1-hexene process according to embodiments herein begins with the initial production of an exclusive 2-pentene (without 1-pentene) stream, which may also include some 3-hexene from an n-butenes feed stream. The 2-pentene is then further reacted via self-metathesis (autometathesis) in a metathesis reactor to selectively form 3-hexene. All formed 3-hexene is separated and further isomerized in a double-bond isomerization-only reactor (reactor 3) to produce an equilibrium mixture of hexenes (1-, 2-, and 3-hexenes). The 1-hexene product is then finally separated via a superfractionator.

Figure 7:
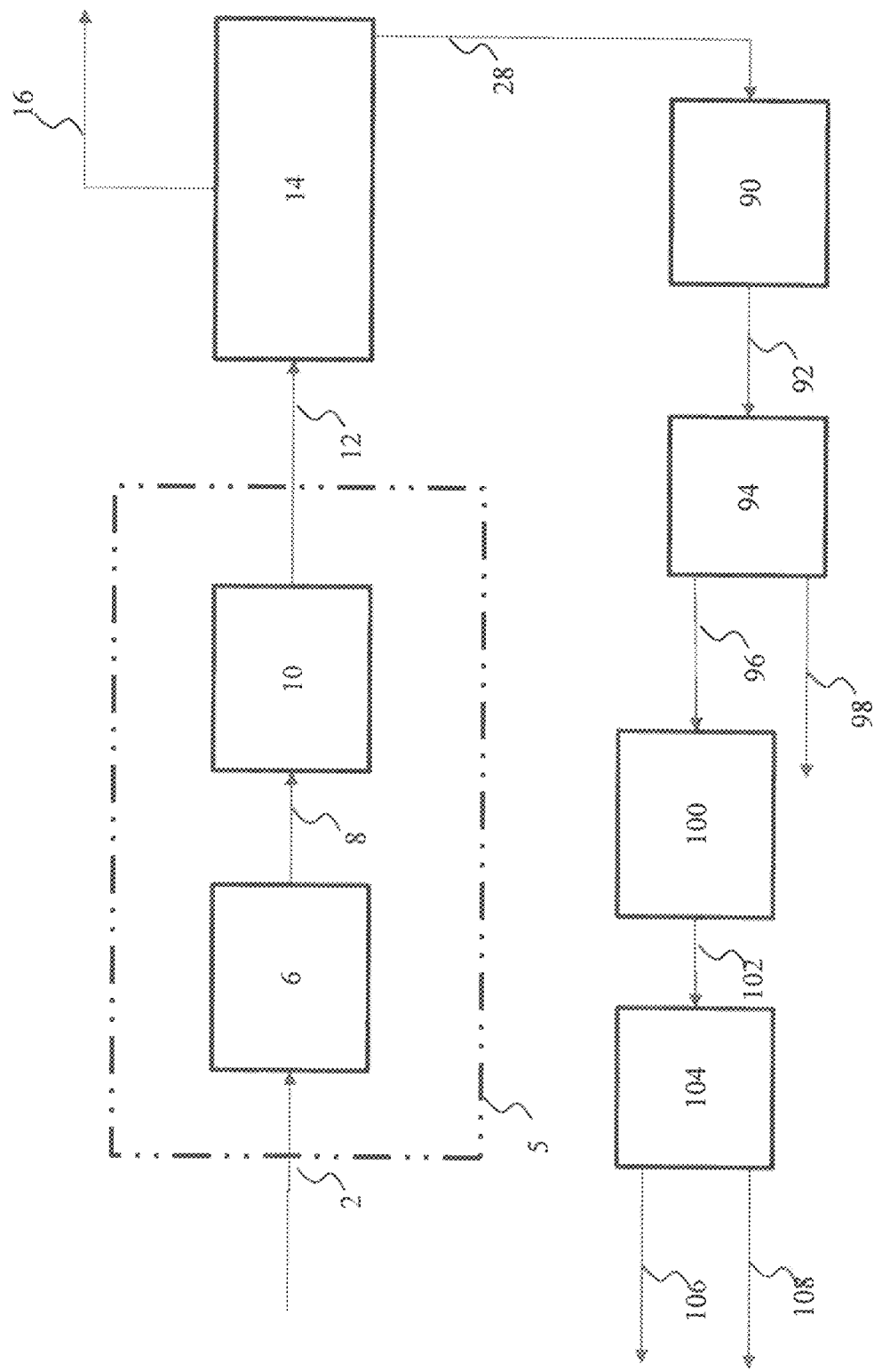
FIG. 7 is a simplified process flow diagram of a process for producing high purity 1-butene according to embodiments disclosed herein.

Referring now to FIG. 7, a simplified process flow diagram of a process for producing 1-hexene according to embodiments herein is illustrated, where like numerals represent like parts. Similar to the 1-butene process, as described above, an exclusive 2-pentene (without 1-pentene) stream 12 is produced from any n-butenes feed stream 2 via reaction in reaction zone 5. A simple fractionation system 14 may then be used to separate the propylene fraction 16 from the 2-pentene fraction 28

To produce 1-hexene, the 2-pentene product stream 28 may be further reacted via self-metathesis (autometathesis) in a metathesis reactor 90 to selectively form a product stream 92 including 3-hexene and 2-butene. The metathesis product 92 may then be fed to a fractionation system 94 to separate the 3-hexene 96 from the 1-butene 98.

Figure 8:
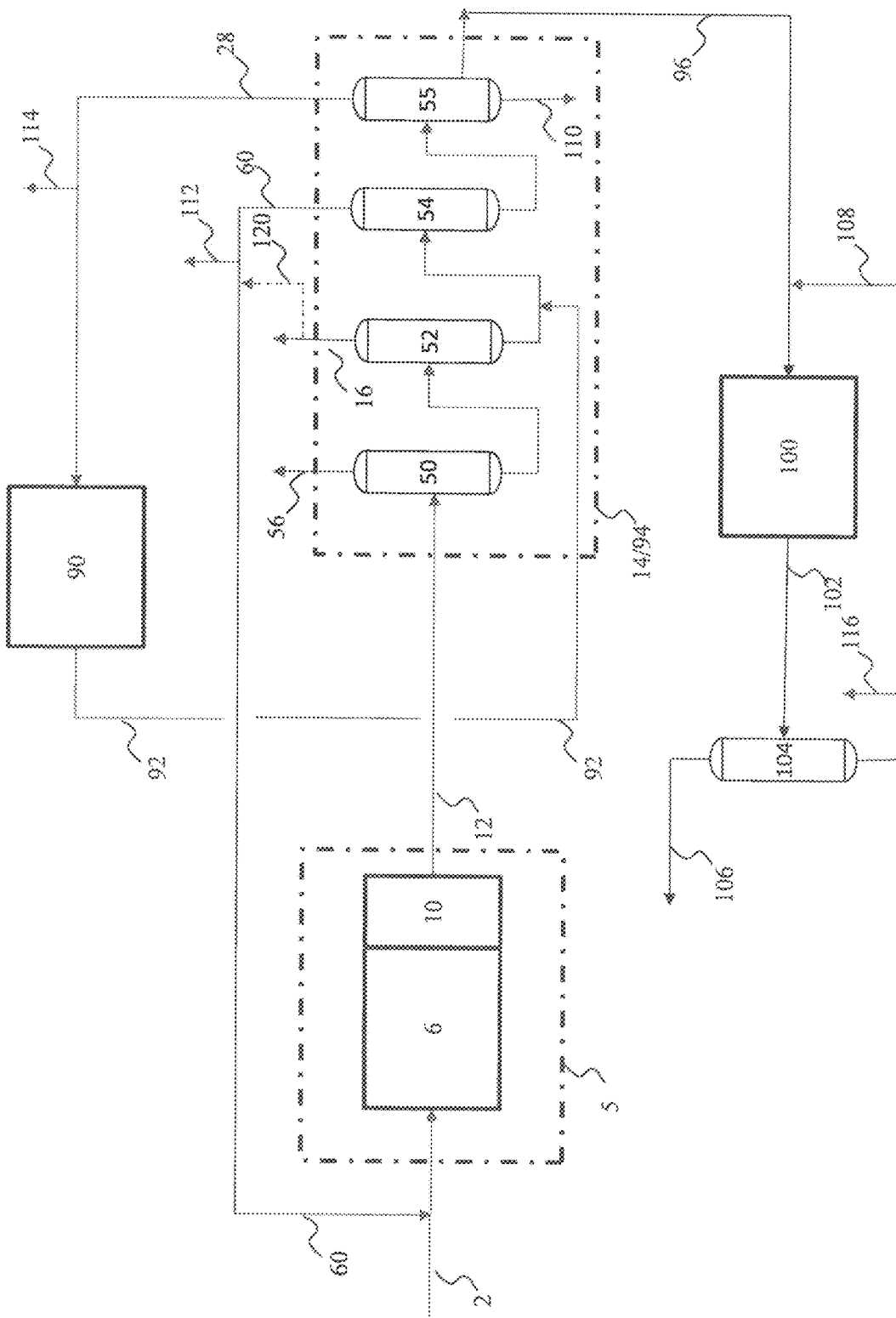
FIG. 8 is a simplified process flow diagram of a process for producing high purity 1-butene according to embodiments disclosed herein.

Following separation, the 3-hexene fraction 96 may be fed to an isomerization reactor 100 for the double-bond isomerization of 3-hexene to form an effluent 102 including positional isomers 1-hexene and 2-hexene as well as unreacted 3-hexene. The effluent 102 may then be separated in a fractionation system 104 to recover a 1-hexene fraction 106 and a 2-hexene and 3-hexene fraction 108. In some embodiments, the effluents from the isomerization/metathesis reaction zone 5 and the metathesis reaction zone 90 may be fed to a common fractionation system 14/94, such as shown in FIG. 8.

The sole feed for this process is an n-butenes stream 2, which may be free of branched C4 species. The n-butenes feed stream may be fed to an isomerization/metathesis reaction zone including an upstream isomerization reaction zone and a downstream reaction zone, producing an effluent including target products 2-pentene and propylene, as well as byproducts ethylene and 3-hexene as well as any unreacted n-butenes.

In the upstream double-bond isomerization reaction zone, double-bond isomerization of the n-butenes is the only reaction (Reaction 8) that occurs, and provides an equilibrium mixture of n-butenes at the starting point of the downstream metathesis reaction zone.

1-Butene←→2-butene    (Reaction 8)

In the downstream metathesis reaction zone 10, the following reactions occur that produces 2-pentene.

1-Butene+2-Butene←→2-Pentene+Propylene    (Reaction 9)

1-Butene+1-Butene←→Ethylene+3-Hexene    (Reaction 10)

The main by-products of ethylene and propylene form via Reactions 9 and 10 and may be recovered from the isomerization/metathesis reaction effluent in a fractionation system as separate product streams. For example, the separation train may include a deethylenizer, a depropylenizer, a debutenizer, and a depentenizer. The separated 2-pentene stream may be fed to a metathesis-only reactor to form a 3-hexene product via autometathesis. These reactions can be written as follows.

2-pentene+2-pentene←→3-hexene+2-butene    (Reaction 11)

The effluent stream from the metathesis reactor, containing 3-hexene, 1-butene and unreacted 2-pentene, may then be re-routed and added to the depropylenizer bottoms streams, which allows the 1-butene and 2-pentene streams to be recycled and separate the 3-hexene to be further processed downstream. All formed 3-hexene is separated from the depentenizer bottoms stream that is sent to a double-bond isomerization-only reactor. The 3-hexene is isomerized to produce an equilibrium mixture of hexenes (1-, 2-, and 3-hexenes) via reactions 12 and 13.

3-Hexene←→2-Hexene    (Reaction 12)

2-Hexene←→1-Hexene    (Reaction 13)

The 1-hexene product is then finally separated via a superfractionator. Depending on the isobutene in the fresh n-butenes fed to the unit, purges may be taken in each of the C4, C5, and C6 recycle streams to prevent isobutene, isopentene and isohexene buildup. These purge streams also allow to prevent buildup of any C4, C5, and/or C6 alkanes that have been introduced with the original mixed butenes containing feed.

One embodiment for the overall process to produce high purity 1-hexene may be as illustrated in FIG. 8, where like numerals represent like parts. As described above, feed butenes 2, which may be a mixture of normal butenes, pure 1-butene, or pure 2-butene, may be fed to reaction zone 5, including an isomerization zone 6 and a segregated metathesis zone 10, for producing an isomerization/metathesis product 12 including 2-pentene and propylene, as well as some by-product ethylene and 3-hexene.

The isomerization/metathesis product 12 may then be fed to a common fractionation system 14/94 for separation of the products, byproducts, and unreacted reactants (normal butenes). Fractionation system 14 may include a deethylenizer 50, a depropylenizer 52, a debutenizer 54, and a depentenizer 55. The deethylenizer 50 may be used to separate an ethylene fraction 56 from heavier hydrocarbons. The depropylenizer 52 may be used to recover a propylene fraction 16. The debutenizer 54 may be used to separate a C4 fraction 60. The depentenizer 55 may be used to separate a 2-pentene fraction 28, recovered as an overheads, from a 3-hexene fraction 96, recovered as a side draw, and a C6+ purge 110, recovered as a bottoms fraction.

The 2-pentene fraction 28 may then be fed to metathesis reaction zone 90. In metathesis reaction zone 90, the 2-pentene may react with itself via autometathesis to produce 2-butene and 3-hexene. Effluent 92 may thus include 3-hexene (target product), 2-butene, as well as unreacted 2-pentene. The effluent 92 from metathesis reaction zone 90 may then be fed to common fractionation zone 14/94, such as intermediate to debutenizer 54, for separation and recovery of the 3-hexene from the lighter components as described above.

Following separation, the 3-hexene fraction 96 may be fed to an isomerization reactor 100 for the double-bond isomerization of 3-hexene to form an effluent 102 including positional isomers 1-hexene and 2-hexene as well as unreacted 3-hexene. The effluent 102 may then be separated in a superfractionation system 104 to recover a 1-hexene fraction 106 and a 2-hexene and 3-hexene fraction 108, which may be recycled to isomerization reactor 100 for additional conversion of the 2- and 3-isomers to 1-hexene. As necessary, a C4 purge 112, a C5 purge 114, and a C6 purge 116 may be withdrawn from the system.

In some embodiments, it may be desirable to recycle a portion of propylene stream 16 back to reaction zone 5, such as via stream 120. The recycled propylene may react with the 1-butene present in the reactor to produce additional 2-pentene within the reaction zones.

While described above with respect to production of high purity 1-butene (and/or propylene) or 1-hexene, other potential uses for the very high purity 2-pentene stream may be considered. For example, the high purity 2-pentene stream produced from a segregated olefins conversion unit using n-butenes as feed could also be used to produce isoprene, such as via a 2-methyl-2-pentene intermediate formed from 2-pentene reacted with isobutene, described in US 2011/0034747, which is incorporated herein by reference in its entirety.

As described above, processes for the production of olefins according to embodiments herein may include: contacting a hydrocarbon mixture comprising linear butenes with an isomerization catalyst to form an isomerization product comprising 2-butenes and 1-butenes; contacting the isomerization product with a first metathesis catalyst to form a first metathesis product comprising 2-pentene and propylene, as well as any unreacted $C_4$ olefins, and byproducts ethylene and 3-hexene; fractionating the first metathesis product to form a C3-fraction and a C5+ fraction comprising 2-pentene, which may be a high purity 2-pentene fraction.

For the production high purity 1-butene, the process may also include contacting ethylene and the C5+ fraction with a second metathesis catalyst, which may be the same or different than the first metathesis catalyst, to convert at least a portion of the 2-pentene and ethylene to propylene and 1-butene and form a second metathesis product. The second metathesis product may then be readily fractionated to recover a propylene fraction and a high purity 1-butene fraction. In some embodiments, the 1-butene fraction may have a purity of at least 98 wt % 1-butene. In other embodiments, the 1-butene fraction may have a purity of at least 98.5 wt %, at least 99 wt %, or at least 99.5 wt % 1-butene.

For the production of high purity 1-hexene, the process may also include contacting the C5+ fraction with a second metathesis catalyst, which may be the same or different than the first metathesis catalyst, to convert at least a portion of the 2-pentene to 2-butene and 3-hexene and form a second metathesis product. The second metathesis product may then be readily fractionated to recover a 2-butene fraction and a 3-hexene fraction. The 3-hexene fraction has a purity of at least 98 wt % 3-hexene. In some embodiments, the 3-hexene fraction may have a purity of at least 98 wt % 3-hexene. In other embodiments, the 3-hexene fraction may have a purity of at least 98.5 wt %, at least 99 wt %, or at least 99.5 wt % 3-hexene. The 3-hexene may then be converted via isomerization to 1-hexene.

In embodiments disclosed herein, the isomerization/metathesis reactor 5, 6, 10, and/or the metathesis reactors 24, 90 may be operated at a pressure between 2 and 40 atmospheres, and between 5 and 15 atmospheres in other embodiments. The reactors may be operated such that the reaction temperature is within the range from about 50° C. to about 600° C.; within the range from about 200° C. to about 450° C. in other embodiments; and from about 250° C. to about 400° C. in yet other embodiments. The isomerization and metathesis reactions may be performed at a weight hourly space velocity (WHSV) in the range from about 2 to about 200 in some embodiments, and from about 6 to about 40 in other embodiments.

The reactions may be carried out by contacting the olefin(s) with the isomerization and/or metathesis catalysts in the liquid phase or the gas phase, depending on structure and molecular weight of the olefin(s). If the reaction is carried out in the liquid phase, solvents or diluents for the reaction can be used. Aliphatic saturated hydrocarbons, e.g., pentanes, hexanes, cyclohexanes, dodecanes and aromatic hydrocarbons such as benzene and toluene are suitable. If the reaction is carried out in the gaseous phase, diluents such as saturated aliphatic hydrocarbons, for example, methane, ethane, propane, normal and branched C4, C5, alkanes and/or substantially inert gases, such as nitrogen and argon, may be present. For high product yield, the reactions may be conducted in the absence of significant amounts of deactivating materials such as water and oxygen.

The contact time needed to obtain a desirable yield of reaction products depends upon several factors such as the activity of the catalyst, temperature, pressure, and the structure of the olefin(s) to be isomerized and/or metathesized. Length of time during which the olefin(s) are contacted with catalyst can vary between 0.1 seconds and 4 hours, preferably from about 0.5 sec to about 0.5 hrs. The isomerization and metathesis reactions may be conducted batch-wise or continuously with fixed catalyst beds, slurried catalyst, fluidized beds, or by using any other conventional contacting techniques.

The catalyst contained within the metathesis reactor may be any known metathesis catalyst, including oxides of Group VIA and Group VIIA metals on supports. Catalyst supports can be of any type and could include alumina, silica, mixtures thereof, zirconia, magnesia, titanic, and zeolites. In some embodiments, the metathesis catalyst is tungsten oxide on silica.

The double bond isomerization catalyst may be any known double bond isomerization catalyst. In some embodiments, the double bond isomerization catalyst may be one of magnesium oxide, calcium oxide, aluminum oxide, or mixed Mg—Al oxides (e.g, hydrotalcite-derived mixed oxides), among other possible catalysts.

In some embodiments, the double bond isomerization catalyst may be an alumina-titania catalyst. The catalyst may be a γ-alumina-titanic crystalline mixture including active sites that catalyze the positional isomerization of olefins, and may be in the form of pellets, extrudates, and the like, and will typically have an effective diameter of 0.5 mm to 5 mm, such as in the range from 1 mm to 4 mm, or in the range from 2 mm to 3 mm. In some embodiments, the alumina-titania catalyst may have a composition of titanium with a lower limit of 0.01, 1, 2, 3, 4, 5, 10, 15, 20, or 25 to an upper limit of 15, 20, 25, 30, 35, 40, 45, or 50 wt %, where any lower limit may be combined with any upper limit. γ-Alumina-titania catalyst herein may have a surface area in some embodiments greater than 200 m$^2$/g, in other embodiments greater than 250 m$^2$/g, in other embodiments greater than 300 m$^2$/g, in other embodiments greater than 350 m$^2$/g, and in other embodiments greater than 400 m$^2$/g. The γ-alumina-titania catalysts may be tolerant of oxygenated species that are typically considered a poison, such as to MgO type catalysts, may act as an oxygenate scavenger protecting downstream catalyst beds, and in some embodiments may have activity for dehydration of alcohols in addition to isomerization activity. The γ-alumina-titanic catalysts may also be more forgiving with respect to cyclopentene purity of the feed, and may allow greater than 5 wt %, greater than 7.5 wt %, or even greater than 10 wt % cyclopentene to be present in the feed, potentially negating typical upstream processes required to remove cyclopentene from the feed. These γ-alumina-titania catalysts may be used alone, such as in an isomerization only reactor or in an isomerization catalyst bed in a segregated OCU, or may be used in admixture with other isomerization catalysts or metathesis catalysts.

EXAMPLES

Figure 9:
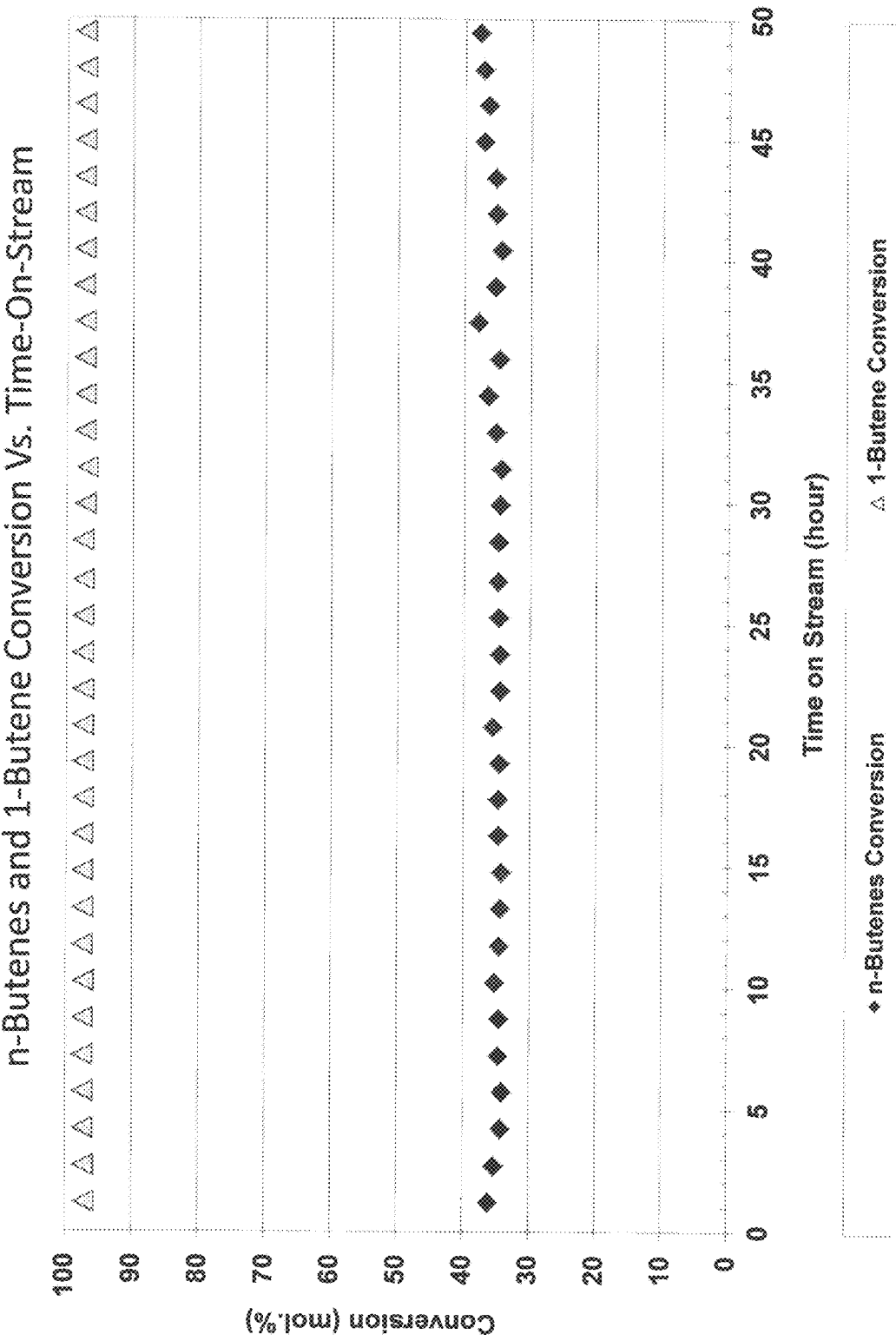
FIG. 9 is a plot illustrating 1-butene and n-butene conversion during experiments operating a process according to embodiments herein.
Figure 10:
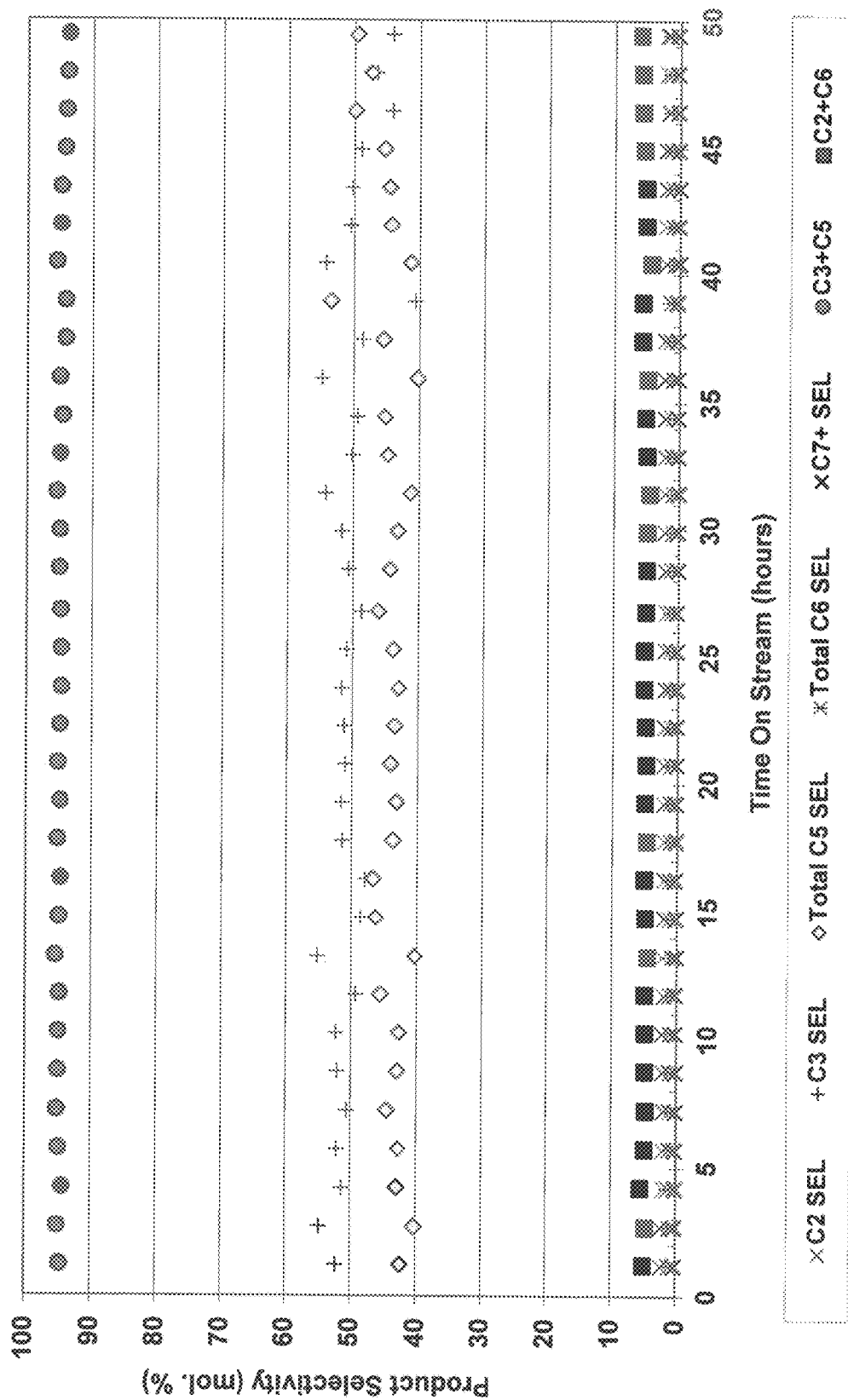
FIG. 10 is a plot illustrating product selectivity during experiments operating a process according to embodiments herein.
Figure 11:
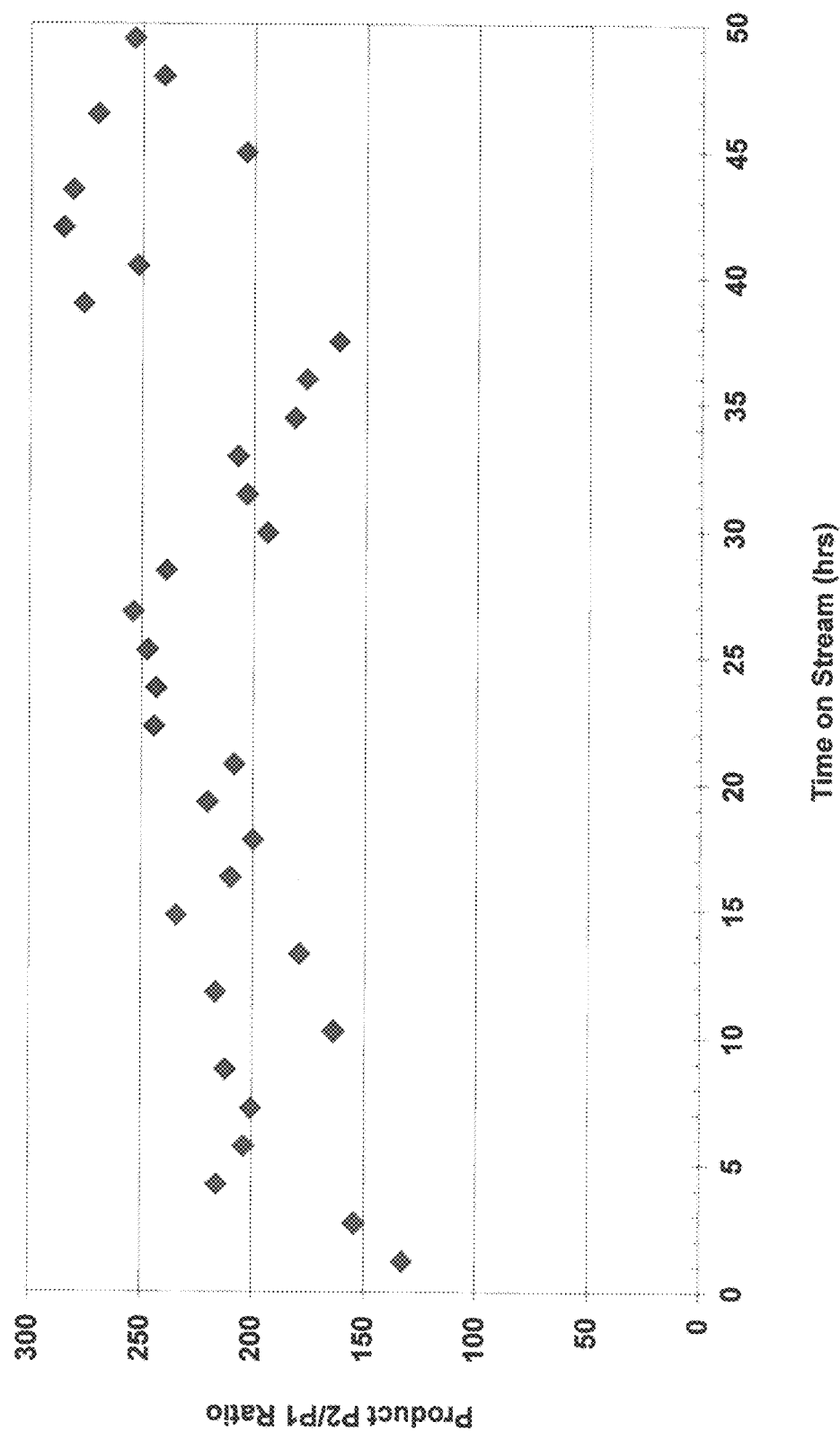
FIG. 11 is a plot illustrating 2-pentene to 1-pentene ratios during experiments operating a process according to embodiments herein.

Production of high purity 2-pentene, such as by the process as shown in FIG. 1, was performed. Testing results from the laboratory-scale tests are provided in FIGS. 9-11. This test was performed in a reactor loaded in a "segregated OCU" reactor configuration with an upper catalyst bed of MgO for double-bond isomerization only and a lower catalyst bed for exclusive metathesis activity using a pure 1-butene stream as feed. Four (4) times more MgO catalyst was loaded relative to the metathesis catalyst load to ensure a constant equilibrium n-butenes mixture maintaining a 2-butene to 1-butene ratio of 4 (B2/B1=4) is attained at the starting point of the $WO_3/SiO_2$ catalyst bed. As shown in FIG. 9, very high once through 1-butene conversion levels (>97%) were achieved and maintained 50 hours time-on-stream (TOS). Excellent stable equilibrium product selectivities towards desired products (2-pentenes and propylene) near 95% were achieved at 316° C. (600° F.) and 120 psig as shown in FIG. 10. The 2-pentenes to 1-pentene (P2/P1) ratios of the product stream exhibited a somewhat broad range between 130-285 as shown in FIG. 11.

This data clearly indicates that the pentenes product produced via the segregated OCU reactor configuration produces an almost exclusive mixture of 2-pentenes with very low levels of 1-pentene being formed. The relatively high variability observed in the P2/P1 ratios is mostly due to relatively high errors in GC (gas chromatogram) peak integrations of the very small amounts of 1-pentene present. Furthermore, the results shown here are provided for demonstration of the concept and not fully optimized. Thus, the purity of the 2-pentenes product can be significantly improved from those provided in this example and shown in FIGS. 9-11.

The upper and lower catalyst sections can be either located in a single reactor or two (2) separate reactors in series. For the case of two separate reactors, the first reactor is used to only perform double-bond isomerization, and the second reactor is used exclusively for metathesis of the effluent product stream from the first reactor. Furthermore, each reactor may be operated as a completely separate reactor and thus allowing to operate under different reaction conditions (e.g, different temperatures, pressures, and different WHSV (weighted hourly space velocities) to maximize the yield of product or to reduce overall operational costs.

As described above, embodiments disclosed herein provide for the production of a high purity 2-pentene stream. The high purity 2-pentene stream may then be advantageously used to produce end products such as isoprene, high purity 1-butene, and high purity 1-hexene.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A system for the production of olefins, the system comprising:
an isomerization/metathesis reaction system for:
contacting a hydrocarbon mixture comprising linear butenes with an isomerization catalyst to form an isomerization product comprising 2-butenes and 1-butenes; and
contacting the isomerization product with a first metathesis catalyst to form a first metathesis product comprising 2-pentene and propylene, as well as any unreacted $C_4$ olefins, and byproducts ethylene and 3-hexene;
a fractionation system for fractionating the first metathesis product to form an ethylene fraction, a propylene fraction, a C4 fraction and a C5 fraction comprising 2-pentene as essentially the only C5 olefin;
a flow conduit for feeding at least a portion of the propylene fraction to the isomerization/metathesis reaction system; and
a metathesis reactor for contacting ethylene and the C5 fraction with a second metathesis catalyst, which may be the same or different than the first metathesis catalyst, to convert at least a portion of the 2-pentene and ethylene to propylene and 1-butene and form a second metathesis product.

2. The system of claim 1, wherein the flow conduit for recycling the propylene fraction is configured to introduce the propylene fraction upstream of the isomerization catalyst, upstream of the first metathesis catalyst, or both.

3. The system of claim 1, further comprising a second fractionation system for fractionating the second metathesis product to form a second propylene fraction and a 1-butene fraction.

4. The system of claim 3, further comprising a flow conduit for recycling the second propylene fraction to upstream of the isomerization catalyst, upstream of the first metathesis catalyst, or both.

5. The system of claim 1, further comprising a metathesis reactor for contacting the C5 fraction with a second metathesis catalyst, which may be the same or different than the first metathesis catalyst, to convert at least a portion of the 2-pentene to 2-butene and 3-hexene and form a second metathesis product.

6. The system of claim 5, further comprising a second fractionation system for fractionating the second metathesis product to form a 2-butene fraction and a 3-hexene fraction.

7. The system of claim 6, further comprising a flow conduit for recycling the 2-butene fraction to the isomerization/metathesis reaction system.

8. The system of claim 6, further comprising an isomerization reactor for converting the 3-hexene fraction via isomerization to 1-hexene.

9. The system of claim 1, further comprising a reaction system for converting the 2-pentene to isoprene.

10. A system for the production of olefins, the system comprising:
an isomerization/metathesis reactor including an inlet, for receiving a mixed C4-olefin stream comprising a mixture of 1-butene and 2-butene, and including a first reaction zone comprising an isomerization catalyst and a second reaction zone comprising a first metathesis catalyst for:
contacting the mixed C4-olefin stream with the isomerization catalyst in the first reaction zone to form an isomerization product comprising 2-butene and 1-butene;

contacting the isomerization product with the first metathesis catalyst in the second reaction zone to form a first metathesis product comprising 2-pentene, propylene, and byproducts ethylene and 3-hexene;

a fractionation system for fractionating the first metathesis product to form at least one C3-fraction and a C5 fraction comprising 2-pentene;

a metathesis reactor for contacting ethylene and the 2-pentene in the C5 fraction with a second metathesis catalyst, which may be the same or different than the first metathesis catalyst, to convert at least a portion of the ethylene and 2-pentene to propylene and 1-butene and recovering a second metathesis product;

a second fractionation system for fractionating the second metathesis product to recover a propylene fraction and a 1-butene fraction; and a flow conduit for feeding at least a portion of the propylene fraction to the isomerization/metathesis reactor.

11. A system for the production of olefins, the system comprising:

an isomerization/metathesis reactor including an inlet, for receiving a mixed C4-olefin stream comprising a mixture of 1-butene and 2-butene, and including a first reaction zone comprising an isomerization catalyst and a second reaction zone comprising a first metathesis catalyst for:

contacting the mixed C4-olefin stream with the isomerization catalyst in the first reaction zone to form an isomerization product comprising 2-butene and 1-butene;

contacting the isomerization product with the first metathesis catalyst in the second reaction zone to form a first metathesis product comprising 2-pentene, propylene, and byproducts ethylene and 3-hexene;

a fractionation system for fractionating the first metathesis product to form an ethylene fraction, a propylene fraction, a C4 fraction and a C5+ fraction comprising 2-pentene and 3-hexene;

a metathesis reactor for contacting ethylene and the C5+ fraction with a second metathesis catalyst, which may be the same or different than the first metathesis catalyst, to convert at least a portion of the ethylene and 2-pentene to propylene and 1-butene and to convert at least a portion of the 3-hexene and ethylene to 1-butene and recovering a second metathesis product;

a flow conduit for feeding the second metathesis product to the fractionation system; and a flow conduit for feeding the propylene fraction to the isomerization/metathesis reactor.

12. The system of claim 11, further comprising a flow conduit for feeding at least a portion of the C4 fraction to the isomerization/metathesis reactor.

13. The system of claim 11, wherein the fractionation system comprises a depropylenizer column, and wherein the depropylenizer column comprises a side draw for recovering the C4 fraction.

* * * * *